US010883085B2

(12) United States Patent
Wu et al.

(10) Patent No.: US 10,883,085 B2
(45) Date of Patent: Jan. 5, 2021

(54) PRRSV SX-105 STRAIN AND USE THEREOF

(71) Applicant: Institute of Animal Science and Veterinary Medicine, Shandong Academy of Agricultural Sciences, Shandong (CN)

(72) Inventors: Jiaqiang Wu, Shandong (CN); Jiang Yu, Shandong (CN); Yuyu Zhang, Shandong (CN); Xiwang Zhu, Shandong (CN); Yijun Du, Shandong (CN); Jun Li, Shandong (CN); Xiaoyan Cong, Shandong (CN); Jinbao Wang, Shandong (CN)

(73) Assignee: Institute of Animal Science and Veterinary Medicine, Shandong Academy of Agricultural Sciences, Shandong (CN)

( * ) Notice: Subject to any disclaimer, the term of this patent is extended or adjusted under 35 U.S.C. 154(b) by 538 days.

(21) Appl. No.: 14/917,010

(22) PCT Filed: Jan. 29, 2015

(86) PCT No.: PCT/CN2015/000059
§ 371 (c)(1),
(2) Date: Mar. 6, 2016

(87) PCT Pub. No.: WO2016/119079
PCT Pub. Date: Aug. 4, 2016

(65) Prior Publication Data
US 2018/0371424 A1  Dec. 27, 2018

(51) Int. Cl.
*A61K 39/12* (2006.01)
*A61K 39/00* (2006.01)
*C12N 7/00* (2006.01)
*C07K 14/005* (2006.01)
*A61K 38/00* (2006.01)
*A61P 31/14* (2006.01)

(52) U.S. Cl.
CPC ............. *C12N 7/00* (2013.01); *A61K 39/12* (2013.01); *A61P 31/14* (2018.01); *A61K 2039/5254* (2013.01); *A61K 2039/543* (2013.01); *A61K 2039/545* (2013.01); *A61K 2039/552* (2013.01); *C12N 2770/10021* (2013.01); *C12N 2770/10034* (2013.01); *C12N 2770/10064* (2013.01)

(58) Field of Classification Search
CPC .............. A61K 39/12; A61K 2039/552; A61K 2039/5254; C12N 2770/10034; C12N 7/00
See application file for complete search history.

(56) References Cited

FOREIGN PATENT DOCUMENTS

| CN | 101220348 | 7/2008 |
|---|---|---|
| CN | 101307305 | 11/2008 |
| CN | 101633909 | 1/2010 |
| CN | 102304496 | 1/2012 |

OTHER PUBLICATIONS

Jinqiang Zhang et al., Molecular characteristics of complete genome of a Shandong mutant strain of porcine reproductive and respiratory syndrome virus SX-1, Chin. J. Vet. Sci., Mar. 31, 2011, vol. 31 No. 3, ISSN 1005-4545, pp. 309-314.

Jinqiang Zhang et al.,Isolation of PRRSV SX-1 strain and Clone and Mutation Analysis of Its Nsp2 and ORF5 Gene, Acta Ecologiae Animalis Domastici, Sep. 30, 2009, vol. 30 No. 5. ISSN 1004-5228, pp. 24-28.

Jiaqiang Wu et al., PRRSV SX-1 strain isolation and clone and mutation analysis of ORF 5 and ORF7 gene, 7th National Members' Representative Convention of Infectious Disease of Domestic Animals Branch of Chinese Association of Animal Science and Veterinary Medicine and its 13th Symposium Papers Collection (vol. 1), Dec. 31, 2009.

Sufang Cao et al., Genetic Analysis of the ORF5 Genes of Two Henan Highly Pathogenic PRRSV Isolates, Henan Agricultural Sciences, Jul. 31, 2009, No. 7, ISSN 1004-3268, pp. 114-119.

*Primary Examiner* — Barry A Chestnut

(57) ABSTRACT

The present invention relates to porcine reproductive and respiratory syndrome virus (PRRSV) vaccines in a field of veterinary biological products, and more particularly to a PRRSV SX-105 strain having a deposit number of CGMCC No. 9906, and a use thereof in preparing PRRSV live vaccines. PRRSV SX-1 original strains are strongly pathogenic to swine. A PRRSV SX-105 attenuated strain shows safety and good immunogenicity on the swine. The PRRSV live vaccines, prepared from the PRRSV SX-105 strain, are safe and reliable, and able to generate strong immunity after immunization. The PRRSV live vaccines significantly decrease morbidity and mortality in inoculated swine groups, and have immunization effects reaching and slightly better than conventional commercial vaccines on the market, showing advantages to compete with the same kind of products around the world. The PRRSV live vaccines are capable of effectively preventing PRRS epidemic and transmission, and has broad application prospects.

5 Claims, No Drawings

Specification includes a Sequence Listing.

PRRSV SX-105 STRAIN AND USE THEREOF

CROSS REFERENCE OF RELATED APPLICATION

This is a U.S. National Stage under 35 U.S.C 371 of the International Application PCT/CN2015/000059, filed Jan. 29, 2015.

BACKGROUND OF THE PRESENT INVENTION

Field of Invention

The present invention relates to porcine reproductive and respiratory syndrome virus (PRRSV) vaccines in a field of veterinary biological products, and more particularly to a PRRSV SX-105 strain and a use of the PRRSV SX-105 strain.

Description of Related Arts

The porcine reproductive and respiratory syndrome (PRRS), also known as "swine blue-ear disease", is induced by the porcine reproductive and respiratory syndrome virus (PRRSV). The PRRSV infection may cause the sow abortion, returning to mate, the stillbirth or weak piglet, the dead piglet and the different degrees of respiratory tract symptoms of different-aged swine, while the PRRSV infection also can cause the immunosuppression, the secondary infection or the immunization failure of other diseases. In 1987, the United States of America reported the disease for the first time, and the disease rapidly spread all over the America. In the few years since 1987, the disease has rapidly spread all over the world. The end of 1995 witnessed the disease outbreak in China, and the rapid spread among several provinces of China. Many scaled swine farms had the very high PRRS positive rate, and the PRRS positive rate in some farms was more than 80%. Since 2006, the highly pathogenic PRRS (HP-PRRS), induced by the PRRSV variant strain (the Nsp2 protein lacking 30 amino acids), emerged on the swine farms in partial regions of China. Clinically, the HP-PRRS was mainly characterized by the symptoms of high fever, dyspnea and skin redness, higher morbidity and mortality, causing the extremely serious economic loss in the swine industry in China.

There has been no special treatment drug for the PRRS yet. It is difficult to control the disease once outbreak. Therefore, it mainly depends on the comprehensive precaution measures to control the incidence and transmission of the disease. The PRRSV inactivated vaccine and the PRRSV attenuated vaccine play a leading role in the PRRS precaution. Because the antigen diversity widely exists between each PRRSV isolate, the cross protection of the antigen between different strains is limited, so that the conventional commercial vaccines are merely able to control the PRRS transmission and spread to certain extent. Therefore, it is urgent to provide a PRRSV strain which has good cross protection and strong immunogenicity, and a use of the PRRSV strain in preparing highly-efficient PRRSV vaccines for PRRSV prevention and control.

SUMMARY OF THE PRESENT INVENTION

An object of the present invention is to provide a PRRSV SX-105 strain having strong immunogenicity, to solve the weak immune protection of the conventional PRRSV commercial vaccines worldwide.

Another object of the present invention is to provide a use of the PRRSV SX-105 strain in preparing an attenuated vaccine with strong immune protection.

Accordingly, in order to accomplish the above objects, the present invention provides the following technical solutions.

A PRRSV SX-105 strain, having a Deposit Number of CGMCC No. 9906.

A method for preparing a PRRSV live vaccine, comprising using the PRRSV SX-105 strain.

Preferably, the PRRSV live vaccine is prepared from an attenuated strain, which has virulence significantly weakened and good immunogenicity, the attenuated strain being a $105^{th}$ passage from a PRRSV SX-1 strain continuously passage-cultured on Marc-145 cells. The attenuated strain is a PRRSV SX-105 attenuated strain.

Preferably, the PRRSV live vaccine is a freeze dried vaccine.

Each dose of the freeze dried vaccine has a virus content $\geq 10^{5.0}$ TCID$_{50}$.

The present invention has the following benefits. The PRRSV SX-1 primary strain shows a strong pathogenicity on the swine. On the contrary, the PRRSV SX-105 attenuated strain shows security and good immunogenicity on the swine. It is secure and reliable to prepare a live vaccine from the PRRSV SX-105 attenuated strain. An immunization with the live vaccine is capable of generating strong immunity, and significantly decreasing morbidity and morality of vaccinated swine groups. The live vaccine prepared from the PRRSV SX-105 attenuated strain has immunity effects reaching and slightly better than conventional commercial vaccines on the market, showing advantages to compete with the same kind of products around the world. The live vaccine prepared from the PRRSV SX-105 attenuated strain is capable of effectively preventing PRRS epidemic and transmission and reducing economic loss caused by PRRS, and thus has broad application prospects.

Strain Deposit Information

Deposit Time: Oct. 30, 2014

Deposit Center: China General Microbiological Culture Collection Center (CGMCC)

Deposit Number: CGMCC No. 9906

Deposit Address: Institute of Microbiology Chinese Academy of Sciences, 3# No. 1 West Beichen Road, Chaoyang District, Beijing Class Name: Porcine reproductive and respiratory syndrome virus

DETAILED DESCRIPTION OF THE PREFERRED EMBODIMENT

These and other objectives, features, and advantages of the present invention will become apparent from the following detailed description and the appended claims.

Example 1

PPRSV SX-105 strain, Deposit Number CGMCC No. 9906, deposited at China General Microbiological Culture Collection Center 1.1 PPRSV Strain Isolation and Plaque Clone Purification 1.1.1 Sample Collection and Treatment Dissecting suspected PRRS piglets, aged 7-10 days, from a large-scaled swine farm in Shandong Province of China, to collect lung and blood serum; homogenate grinding; preparing the lung and blood serum into a 10% suspension solution through dulbecco's modified eagle medium (DMEM); adding a penicillin-streptomycin solution to the 10% suspension solution, and then centrifuging at 2000 r/min for 30 min; taking a supernatant after centrifuging, and processing the supernatant with bacteria removal by 0.22 μm microfiltration membrane; freezing the supernatant at −70° C. for storage.

1.1.2 Virus Isolation

After the above collection and treatment, the sample was inoculated on Marc-145 cells which has developed into a single layer; absorbing at 37° C. for 1 h, and then abandoning virus inoculation liquid; rinsing in a phosphate buffered saline (PBS), and then adding DMEM containing 2% newborn calf serum (NBCS); culturing in a 5% $CO_2$ incubator at 37° C. for 5-7 days, and observing cell states every day. Finding a cytopathic effect (CPE) on a $3^{rd}$ blind passage, and then harvesting virus.

1.1.3 Plaque Clone Purification

Processing a virus culturing solution with 10× series dilution, and then respectively inoculating the virus culturing solution on Marc-145 cells which has developed into a single layer; absorbing at 37° C. for 1 h; rinsing twice in serum-free DMEM, and then covering on 0.75% agarose gel containing DMEM; culturing in 5% $CO_2$ incubator at 37° C. for 3-4 days; staining with 0.1% neural red for 5-7 h. Observing white plaque in a red brown background; selecting out monoclonal plaques for virus clone purification, named as SX-1 strains.

1.2 Reverse Transcription-Polymerase Chain Reaction (RT-PCR) Identification 1.2.1 Primer Design Designing a first pair of primers according to a sequence of a PRRSV American Type Culture Collection (ATCC) VR-2332 strain (GenBank No: U87392.3), wherein: a forward primer PSF: 5'-AGGTGGGCAACTGTTTTAGC-3'; a reverse primer PSR: 5'-TTTGTGGAGCCGTGCTATCA-3'; the first pair of primers were synthesized in Shanghai Biological Engineering Co., Ltd. The first pair of primers amplified a specific segment, 697 bp long, of PRRSV ORF5 gene.

1.2.2 Virus RNA Template Preparation

After harvesting the virus, processing the virus with freezing and thawing for 3 times, centrifuging at 8000 r/min for 15 min, and taking a supernatant after centrifuging; extracting virus total RNA with a Trizol kit, from the supernatant; dissolving the virus total RNA with sterilized ultrapure water, and storing at −80° C.

1.2.3 RT-PCR Amplification and Product Sequence Analysis

Executing a one-step RT-PCR amplification with a Prime Script One Step RT-PCR kit, comprising steps of: mixing 3 μL of the virus RNA template, 12.5 μL of 2×1 Step Buffer, 1 μL of the forward primer and 1 μL of the reverse primer (10 μmol/L), with 1 μL of Prime Script 1 Step Enzyme Mix, so as to obtain a mixture; adding water to the mixture to 25 μL; reversely transcribing at 50° C. for 30 min; heating at 94° C. for 2 min, followed by 30 cycles of denaturizing at 94° C. for 30 s, annealing at 53° C. for 30 s and extending at 72° C. for 2 min, and finally extending at 72° C. for 10 min, so as to obtain a PCR product; observing a specific band which is 697 bp long, after 1% hemoglobin agarose electrophoresis of the PCR product; gel recovering the specific band to be sequenced by Shanghai Biological Engineering Co., Ltd., so as to obtain a sequence; submitting the obtained sequence to GenBank (EU480736.1) for a Basic Local Alignment Search Tool (BLAST) comparison. Comparison results showed that a homology between the obtained sequence and a PRRSV corresponding sequence reached more than 98%, indicating that the SX-1 strain was the PRRSV strain.

1.3 PRRSV SX-1 Strain Nsp2 Gene Segment Amplification

Designing a second pair of primers for amplifying PRRSV Nsp2 gene segment according to a sequence of a PRRSV JXA1 strain (GenBank No: EF11245.1), PN1 (5'-CGGTTTTGATGGGCGACA-3') and PN2 (5'-TGCAGGCGTGCGAGGTAA-3'), synthesized by Shanghai Biological Engineering Co., Ltd.; amplifying a specific segment of PRRSV Nsp2 gene with the second pair of primers, wherein: PRRSV classic strain amplified segment length 809 bp; PRRSV highly pathogenic strain amplified segment length 719 bp. The PRRSV SX-1 strain Nsp2 gene segment was amplified with a one-step RT-PCR, and an amplification product was processed with 1% hemoglobin agarose electrophoresis. A 719 bp long specific band was observed, which indicates that the SX-1 strain was a PRRSV highly pathogenic strain.

1.4 Immunofluorescence Antibody Assay (IFA)

Preparing a cell culturing plate which had a single layer of cells; inoculating SX-1 strains onto the cell culturing plate 0.1 ml/well, wherein PRRSV ATCC VR2332 control wells and no-virus-inoculated cell control wells were arranged; observing CPE every day. When the CPE began to emerge, abandoning a cell culturing solution; adding 0.1 ml of pre-cooled absolute ethanol to each well, and acting at a room temperature for 10 min. Abandoning the ethanol, drying up naturally, and rinsing in PBS for 3 times; dropwisely adding a PRRSV monoclonal antibody (American type) diluted 1:500, and acting in a humid chamber at 37° C. for 45 min; rinsing in the PBS for 3 times; after drying up, adding fluorescein isothiocyanate-goat anti-mouse (FITC-goat anti-mouse) IgG to stain for 45 min; after rinsing and drying up, observing with a fluorescence microscope. Specific fluorescence was observed in the Marc-145 cell cytoplasm infected with the SX-1 strain and the Marc-145 cell cytoplasm infected with the ATCC VR2332 strain, while no fluorescence was observed in the no-virus-inoculated cells.

1.5 PRRSV SX-1 Strain Titer Test

Culturing Marc-145 cells on a 96 well cell culturing plate; when the Marc-145 cells developed into a single layer, diluting virus solution of a purified primary SX-1 strain respectively $10^{-3}$, $10^{-4}$, $10^{-5}$, $10^{-6}$, $10^{-7}$, $10^{-8}$, $10^{-9}$, and $10^{-10}$, wherein: 8 wells were inoculated 100 μL/well for each dilution; two rows of wells were arranged as a control group. Processing the 96 well cell culturing with a static culture in a 5% $CO_2$ incubator at 37° C. for 3-5 days, and counting a number of wells generating CPE. Based on a calculation in a Reed-Muench method, a titer ($TCID_{50}$) of the primary SX-1 strain was $10^{3.80}TCID_{50}$/ml.

1.6 Animal Regression Experiment 4-5 weeks old healthy piglets, PRRSV antibody negative, were randomly divided into two groups, 5 piglets each group. Inoculating a first group with 2 ml of primary SX-1 strain cell virus through intranasal dripping; inoculating a second group with 2 ml of Marc-145 cell culturing solution through intranasal dripping, wherein the second group, as a control group, was protected from virus inoculation. After inoculating, measuring body temperatures and observing clinical symptoms every day; after 14 days, dissecting the 10 piglets to observe pathological changes. Results showed that, on $2^{nd}$ day after inoculating, the body temperatures of the first group began to increase, 41.8° C. as a highest body temperature; the clinical symptoms included anorexia, depression, tremor, rear limb paralysis, dyspnea, skin cyanosis over ears and body; 2 of the 5 inoculated piglets in the first group died at an end of the experiment. Dissection of the first group witnessed different degrees of the pathological changes in internal organs of the inoculated piglets, such as lung tissue diffuse consolidation in an anthophaein shape, lymph node bleeding and enlargement, splenic marginal necrosis, and heavy bleeding or necrosis in lymph node, particularly in inguinal lymph node. The PRRSV was isolated from serum of the inoculated piglets in the first group. The piglets in the second group (the control group) clinically showed normal; no pathological change was observed in internal organ dissection. The experiment showed that the PRRSV SX-1 strain had a relatively strong pathogenicity.

Example 2

Passage attenuation and plaque purification of PRRSV SX-1 strain; study on biological property of attenuated strain of PRRSV SX-1 strain 2.1 Attenuation of PRRSV SX-1 Strain and Purification of Attenuated Strain The PRRSV SX-1 strain was passaged on Marc-145 cells to a $120^{th}$ passage for attenuation, with a multiple passage technique. A complete genome sequence analysis found out that a complete sequence of nucleotides seldom changed in $100^{th}$-$110^{th}$ passages of the SX-1 strain, which indicated that the $100^{th}$-$110^{th}$ passages of the SX-1 strain were basically stable on the Marc-145 cells. A $102^{nd}$ passage of the SX-1 strain was selected for a titer test, wherein the titer of the $102^{nd}$ passage reached $10^{7.00}$ $TCID_{50}$/ml, indicating a good adaptation of the $102^{nd}$ passage of the SX-1 strain on the Marc-145 cells. Therefore, the $100^{th}$-$110^{th}$ passages of the SX-1 strain were chosen as candidate strains for developing attenuated vaccines.

Virus of the $102^{nd}$ passage of the PRRSV SX-1 strain was treated with 3 times of plaque clone purification. A purified virus of a $105^{th}$ passage was named as PPRSV SX-105.

2.2 RT-PCR Identification of PRRSV SX-105 Strain

Employing the P5F and the P5R as a third pair of primers, employing virus total RNA of the PRRSV SX-105 strain as a template, and executing a one-step RT-PCR to amplify ORF5 gene segments with a Prime Script One Step RT-PCR kit. Amplification product was submitted to Shanghai Biological Engineering Co., Ltd. A homology between a nucleotide sequence of the ORF5 gene of the SX-105 strain, shown as SEQ ID NO: 1 in the sequence listing, and a corresponding virus sequence of a primary SX-1 strain was 96.5%.

2.3 PRRSV SX-105 Strain Titer Test

Diluting PRRSV SX-105 10 times, and respectively inoculating each single layer of Marc-145 cells on a 96 well cell culturing plate with the diluted PRRSV SX-105, followed by a static culture at 37° C. and 5% $CO_2$ for 3-5 days; counting a number of wells generating CPE, and finding out that SX-105 strain $TCID_{50} \geq 10^{7.5} TCID_{50}$/ml based on a calculation in a Reed-Muench method.

2.4 Animal Toxicity Experiment

The 10 healthy piglets, PRRSV antigen and antibody negative, were randomly divided into 2 groups, 5 piglets each group. Inoculating a first group with SX-105 strain (titer of around $10^{6.0}$ $TCID_{50}$/ml), through an intramuscular injection 1 ml/piglet; inoculating a second group with normal Marc-145 cell culturing solution as a control group. Separately raising the two groups under the same conditions, and continuously observing the two groups for 21 days. It was observed that the first group, inoculated with virus, and the control group both had normal body temperature, spirits and appetites, without PRRSV infection clinical symptom.

Results showed that the PRRSV SX-105 strain was not pathogenic for the healthy piglets and was an attenuated strain.

2.5 Immunogenicity Experiment 4-5 weeks old healthy piglets, PRRSV antigen and antibody negative, were randomly divided into two groups, 5 piglets each group. Inoculating the piglets in an immunization group with virus of SX-105 strains through a neck-intramuscular injection, $10^{5.0} TCID_{50}$/titer; and injecting a second group with the same amount of physiological saline as a control group. After 28 days, inoculating all the 10 piglets with PRRSV SX-1 strains, 2 ml of intranasal dripping and 2 ml of intramuscular injection ($10^{5.0} TCID_{50}$/ml) for each piglet; observing the immunization group and the control group continuously for 21 d. Results showed 100% (5/5) protection in the immunization group and 100% (5/5) morbidity in the control group, which indicated that the PRRSV SX-105 had relatively good immunogenicity.

Example 3

Application of PRRSV SX-105 strain in preparing PRRSV live vaccine

Inoculating PRRSV SX-105 strains onto Marc-145 cells; harvesting cell cultures; adding an appropriate protectant; and obtaining PRRSV live vaccines through freeze vacuum drying.

Preferably, a method for preparing PRRSV live vaccines from PRRSV SX-105 strains comprises steps as follows.

3.1 Selecting Virus Strain

Selecting a PRRSV SX-105 strain which has a titer $\geq 10^{7.5} TCID_{50}$/ml to be a virus strain for vaccine preparation, wherein the virus strain is diluted to $10^{6.0}$ $TCID_{50}$/ml, in such a manner that a neck-intramuscular injection of 1 ml/piglet failed to induce partial and whole-body adverse reaction on piglets; while the neck-intramuscular injection of 2 ml of the virus strain ($10^{5.0} TCID_{50}$) had relatively good immunization on the piglets.

3.2 Preparing a Virus Strain for Production

Selecting Marc-145 cells which developed into a single layer and had good morphology; abandoning culturing solution; inoculating the virus strain onto the Marc-145 cells at a percentage of 1%, followed by absorption at 37° C. for 60 min; then adding DMEM containing 2% NBCS. Continuing culture at 37° C., and observing CPE every day; harvesting when the CPE reached 80%; freezing and thawing for 3 times; quantitatively separating and packaging, and storing at −20° C.

3.3 Preparing Virus Solution for Vaccine Preparation

Culturing Marc-145 cells with roller bottles; abandoning culturing solution when the Marc-145 cells developed into a single layer; adding cell maintaining solution containing 1% virus strain solution, followed by absorption at 37° C. for 60 min; then, adding DMEM containing 2% NBCS, and continuing culture at 37° C. After inoculating, observing cell changes and CPE every day; harvesting virus when the CPE reached 80%. Repeating freezing and thawing for 3 times, and then mixing virus suspension solution to be uniform; storing at −20° C. The harvested virus was required to have a content $\geq 10^{7.5} TCID_{50}$/ml. The harvested virus suspension solution was required to be sterile in a sterility test.

3.4 Vaccine Distributing, Separating and Packaging

Transferring the virus suspension solution which was stored at −20° C. transferred to a room temperature to melt; after melting, gently vibrating the virus suspension solution; adding a freeze drying protectant at a ratio of 1:1, and fully mixing up; then quantitatively separating and packaging, at a virus titer ≥$10^{5.0}$TCID$_{50}$ in each dose.

3.5 Freeze Drying

After separating and packaging, rapidly freeze vacuum drying 3.6 PRRSV Live Vaccine Safety Test 4-5 weeks old piglets were selected to receive a neck-intramuscular injection of vaccines, 10 doses for each piglet. After 14 days of observing, no adverse reaction was found on the piglets which were injected with vaccines. Alternatively, 5 sows pregnant for 85-90 days were selected to receive a neck-intramuscular injection of vaccines, 20 doses for each sow. After 14 days of observing, no adverse reaction was found on the sows which were injected with vaccines; the 5 sows had normal delivery.

3.7 PRRSV Live Vaccine Potency Test 3.7.1 Virus Content Determination

Diluting PRRSV live vaccine into 1 dose/ml with serum-free culturing medium, and then further diluting the PRRSV live vaccine into 10× series dilution with a culturing medium containing 2% NBCS, at 6 different dilutions of $10^{-3}$, $10^{-4}$, $10^{-5}$, $10^{-6}$, $10^{-7}$ and $10^{-8}$, or other proper dilutions; respectively inoculating the diluted vaccines onto Marc-145 cells which developed into a single layer, 8 wells for each dilution, 0.1 ml/well, wherein a control group with no inoculation was arranged; continuously observing for 5-7 days, and recording a well number generating CPE under each dilution; counting TCID$_{50}$ in a Reed-Muench method, virus content of each dose ≥$10^{5.0}$TCID$_{50}$.

3.7.2 Immunization Test 5 healthy piglets aged 4-5 weeks, PRRSV antigen and antibody negative, were selected to receive intramuscular injection of vaccines, 1 dose for each piglet. Another 5 healthy piglets aged 4-5 weeks, PRRSV antigen and antibody negative, were selected as a control group and raised under the same conditions. After 28 days, each piglet was inoculated with velogenic virus of PRRSV SX-1, through 2 ml of intranasal dripping and 2 ml of intramuscular injection (virus titer ≥$10^{5.0}$TCID$_{50}$) for each piglet. A continuous observation of 21 days witnessed 100% (5/5) protection over the piglets which received the injection of the vaccines and 100% (5/5) morbidity of the piglets in the control group.

3.7.3 Potency Comparison Test with Products of the Same Kind

Three foreign and Chinese commercial live vaccines, comprising an ATCC VR-2332 strain, a CH-1R strain, and a JXA1-R strain, were respectively denoted as live vaccines 1, 2 and 3. An immunization test with regard to the live vaccines 1, 2 and 3, and a live vaccine SX-105 of the present invention, was executed for a comparison in immunization protection effect of the four different live vaccines. Tested velogenic strains were respectively PRRSV SX-1 strains, JXA1 strains and HuN4 strains.

For each tested velogenic strain, the immunization test randomly chose 25 healthy piglets aged 4-5 weeks, PRRSV antigen and antibody negative, divided into 5 groups, 5 piglets each group. Four groups were respectively intramuscularly injected with the live vaccine 1, the live vaccine 2, the live vaccine 3 and the live vaccine SX-105, one dose for each piglet. One group was non-immunized, as a control group. Each group was raised separately under the same conditions. After 28 days, each group was inoculated with the tested velogenic strain, at a virus titer ≥$10^{5.0}$TCID$_{50}$/ml, 2 ml of intranasal dripping and 2 ml of intramuscular injection for each piglet. Each group was observed every day in aspects of mental states and clinical symptoms, and measured rectal temperature, for 21 days continuously. Then, each group was dissected to observe pathological changes in internal organs.

Table 1 shows results of the immunization tests of the four live vaccines. As showed in Table 1, an immunization protection rate of the SX-105 strain reaches 93.3% (14/15); the three live vaccines 1, 2 and 3 have the immunization protection rates respectively of 53.3%, 53.3% and 80%, indicating that the PRRSV SX-105 live vaccine has immunization effects reaching and slightly better than conventional commercial vaccines of the same kind.

TABLE 1 comparison and analysis of immunization test results of 4 live vaccines

| Tested Velogenic strain | Live vaccine | Vaccine strain | Piglet number | Morbid number | Death number | Protection rate |
|---|---|---|---|---|---|---|
| SX-1 strain | 1 | ATCC VR-2332 | 5 | 2 | 0 | 60% |
| | 2 | CH-1R strain | 5 | 2 | 0 | 60% |
| | 3 | JXA1-R strain | 5 | 1 | 0 | 80% |
| | SX-105 | SX-105 strain | 5 | 0 | 0 | 100% |
| | control | / | 5 | 5 | 1 | 0 |
| JXA1 strain | 1 | ATCC VR-2332 | 5 | 3 | 0 | 40% |
| | 2 | CH-1R strain | 5 | 2 | 0 | 60% |
| | 3 | JXA1-R strain | 5 | 1 | 0 | 80% |
| | SX-105 | SX-105 strain | 5 | 0 | 0 | 100% |
| | control | / | 5 | 5 | 0 | 0 |
| HuN4 strain | 1 | ATCC VR-2332 | 5 | 2 | 0 | 60% |
| | 2 | CH-1R strain | 5 | 3 | 0 | 40% |
| | 3 | JXA1-R strain | 5 | 1 | 0 | 80% |
| | SX-105 | SX-105 strain | 5 | 1 | 0 | 80% |
| | control | / | 5 | 5 | 2 | 0 |

One skilled in the art will understand that the embodiment of the present invention as shown in the drawings and described above is exemplary only and not intended to be limiting.

Thus it can be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A porcine reproductive and respiratory syndrome virus (PRRSV) SX-105 strain, having a deposit number of CGMCC No. 9906.

2. A method for preparing a PPRSV live vaccine, comprising steps of: inoculating the PRRSV SX-105 strain as recited in claim 1 onto Marc-145 cells; harvesting cell cultures; adding a freeze drying protectant; and obtaining the PRRSV live vaccine through freeze vacuum drying.

3. The method, as recited in claim 2, wherein: the PRRSV SX-105 strain is a PRRSV SX-105 attenuated strain which has virulence significantly weakened and good immunogenicity, the PRRSV SX-105 attenuated strain being a $105^{th}$ passage from a PRRSV SX-1 strain continuously passage-cultured on the Marc-145 cells.

4. The method, as recited in claim 2, wherein the PRRSV live vaccine is a freeze dried vaccine.

5. The method, as recited in claim 4, wherein each dose of the freeze dried vaccine has a virus content $\geq 10^{5.0}$ $TCID_{50}$.

* * * * *

SEQUENCE LISTING

<160> NUMBER OF SEQ ID NOS: 5

<210> SEQ ID NO 1
<211> LENGTH: 603
<212> TYPE: DNA
<213> ORGANISM: Unknown

```
<220>  FEATURE:
<223>  OTHER INFORMATION: Porcine reproductive and respiratory syndrome
       virus SX-105 strain

<400>  SEQUENCE: 1 atgttgggga agtgcttgac cgcgtgctgt tgctcgcgat tgcttttttt gtggtgtatc      60
gtgccgttct atcttgctgt gctcgccaac gccagcgaca caacagctc tcatattcag     120 ttgatttata acttaacgct atgtgagctg aatggcgcag attggctggc acaaaatttt    180
gactgggcag tggagacttt tgtcatcttc cccgtgttga ctcacattgt ttcctatgga    240
gcactcacca ccagccattt ccttgacaca gttggtctag ccactgtgtc taccgccgga    300
tattatcacg ggcggtatgt cttgagtagc atttacgcag tctgtgctct ggctgcgctg    360
atttgctttg tcattaggct tgcgaagaac tgcatgtcct ggcgctactc ttgtaccaga    420
tataccaact tccttctgga cactaagggc agactctatc gttggcggtc accgtcatt    480 gtagagaaag ggggtaaggt tgaggtcgaa ggtcacctga tcgacctcaa gagagttgtg    540
cttgatggtt ccgcggcaac ccctttaacc agagtttcag cggaacgatg gggtcgtctc    600
tag                                                                  603

<210>  SEQ ID NO 2
<211>  LENGTH: 20
<212>  TYPE: DNA
<213>  ORGANISM: Artificial Sequence
<220>  FEATURE:
<223>  OTHER INFORMATION: DNA sequence

<400>  SEQUENCE: 2 aggtgggcaa ctgttttagc                                                 20

<210>  SEQ ID NO 3
<211>  LENGTH: 20
<212>  TYPE: DNA
<213>  ORGANISM: Artificial Sequence
<220>  FEATURE:
<223>  OTHER INFORMATION: DNA sequence

<400>  SEQUENCE: 3 tttgtggagc cgtgctatca                                                 20

<210>  SEQ ID NO 4
<211>  LENGTH: 18
<212>  TYPE: DNA
<213>  ORGANISM: Artificial Sequence
<220>  FEATURE:
<223>  OTHER INFORMATION: DNA sequence

<400>  SEQUENCE: 4 cggttttgat gggcgaca                                                   18

<210>  SEQ ID NO 5
<211>  LENGTH: 18
<212>  TYPE: DNA
<213>  ORGANISM: Artificial Sequence
<220>  FEATURE:
<223>  OTHER INFORMATION: DNA sequence

<400>  SEQUENCE: 5 tgcaggcgtg cgaggtaa                                                   18
```